US010107665B2

(12) United States Patent
Hall et al.

(10) Patent No.: US 10,107,665 B2
(45) Date of Patent: Oct. 23, 2018

(54) TOILET WITH FLUSH JET FILL TUBE FLOW METER

(71) Applicants: David R. Hall, Provo, UT (US); Dan Allen, Springville, UT (US); Jared Reynolds, Pleasant Grove, UT (US); Joshua Larsen, Spanish Fork, UT (US); Stephen Davis, Salt Lake City, UT (US); Jared Wagner, Provo, UT (US); Terrece Pearman, Draper, UT (US)

(72) Inventors: David R. Hall, Provo, UT (US); Dan Allen, Springville, UT (US); Jared Reynolds, Pleasant Grove, UT (US); Joshua Larsen, Spanish Fork, UT (US); Stephen Davis, Salt Lake City, UT (US); Jared Wagner, Provo, UT (US); Terrece Pearman, Draper, UT (US)

(*) Notice: Subject to any disclaimer, the term of this patent is extended or adjusted under 35 U.S.C. 154(b) by 9 days.

(21) Appl. No.: 15/336,233

(22) Filed: Oct. 27, 2016

(65) Prior Publication Data
US 2017/0198468 A1 Jul. 13, 2017

Related U.S. Application Data

(60) Provisional application No. 62/280,140, filed on Jan. 19, 2016, provisional application No. 62/276,826, filed on Jan. 9, 2016.

(51) Int. Cl.
*E03D 1/00* (2006.01)
*G01F 23/22* (2006.01)
(Continued)

(52) U.S. Cl.
CPC .............. *G01F 23/22* (2013.01); *A61B 5/021* (2013.01); *A61B 5/208* (2013.01); *A61B 5/4381* (2013.01);
(Continued)

(58) Field of Classification Search
CPC ........... E03D 11/13; E03D 1/34; E03D 5/105; A61B 5/021; A61B 5/4381
(Continued)

(56) References Cited

U.S. PATENT DOCUMENTS 3,751,736 A * 8/1973 Egli .................... E03C 1/05 4/305
6,802,084 B2 * 10/2004 Ghertner ................ E03D 1/00 340/605

(Continued)

*Primary Examiner* — Huyen Le (57) ABSTRACT

The present invention is directed to a toilet that includes a liquid level sensor on the surface of a flush jet fill tube. The liquid level sensor is a noncontact electrical impedance sensor that is an electrical capacitor. The capacitor may be used alone or with other volume sensors to detect volume of materials added to a toilet bowl. Some embodiments include a processor which records data and provides reports that may be clinically useful to assess the user's health status. The temporal nature of the liquid level sensor measurements is particularly useful because urination or defecation may be measured over time. Not only are total volumes detected but rates at which waste is deposited into the toilet during the entire excretion event are detected. These measurements are particularly useful in assessing certain health conditions.

9 Claims, 6 Drawing Sheets

(51) Int. Cl.
    *G05D 7/06*         (2006.01)
    *G01N 33/00*      (2006.01)
    *G01F 23/26*      (2006.01)
    *A61B 5/021*      (2006.01)
    *A61B 5/00*       (2006.01)
    *G01F 23/292*     (2006.01)
    *A61B 5/20*       (2006.01)
    *E03D 11/02*      (2006.01)
    *G06F 19/00*      (2018.01)
    *A61B 10/00*      (2006.01)

(52) U.S. Cl.
    CPC .......... *A61B 5/6891* (2013.01); *A61B 10/007* (2013.01); *A61B 10/0038* (2013.01); *E03D 11/02* (2013.01); *G01F 23/263* (2013.01); *G01F 23/292* (2013.01); *G01N 33/0047* (2013.01); *G05D 7/0635* (2013.01); *G06F 19/00* (2013.01); *A61B 2010/0083* (2013.01)

(58) Field of Classification Search
    USPC ............................................................ 4/314
    See application file for complete search history.

(56) References Cited

U.S. PATENT DOCUMENTS

| | | | |
|---|---|---|---|
| 9,756,297 B1* | 9/2017 | Clements | H04N 7/185 |
| 2008/0250555 A1* | 10/2008 | Gaffey | E03D 11/00 |
| | | | 4/427 |
| 2012/0154169 A1* | 6/2012 | Hoekstra | G07F 17/18 |
| | | | 340/870.01 |
| 2013/0186196 A1* | 7/2013 | Veros | G01F 23/263 |
| | | | 73/304 C |
| 2015/0074893 A1* | 3/2015 | Veros | E03D 5/105 |
| | | | 4/313 |
| 2017/0058500 A1* | 3/2017 | Garrels | E03D 9/038 |

* cited by examiner

TOILET WITH FLUSH JET FILL TUBE FLOW METER

CROSS-REFERENCE TO RELATED APPLICATIONS

This application claims priority to U.S. provisional patent application Ser. No. 62/280,140 filed on Jan. 19, 2016 and U.S. provisional patent application Ser. No. 62/276,826 filed on Jan. 9, 2016, both of which the entire contents is hereby incorporated by reference.

BACKGROUND

Field of the Invention

This invention relates to toilets, and, in particular, toilets capable of detecting the volume of material added to the toilet bowl.

Background of the Invention

In a toilet configured to refill the toilet bowl up to a point that is below a trap way overflow level, a level sensor may record a level change corresponding to a volume of waste deposited in the toilet bowl. Measuring the urination and defecation volumes may be useful for clinical monitoring as well as for at-home health trending and diet monitoring.

Various flow meters have been proposed for measuring the flow of water within the hydrostatic circuit of a toilet. Flow meters in a toilet may be used to measure urine flow rates, track overeating, measure diarrhea volumes, as well as applications for conservation (optimal flush volumes) and clog detection. Typical flow meters assume a full pipe, which is not the case in a toilet, and measure Doppler effects with ultrasound or heat flow with a heater and a temperature sensor. These methods are quite challenging with a porcelain toilet. Others have proposed to place a valve below the trap way which will drain standing water and then measure the volume in time with a liquid level meter and differentiate to obtain flow rates. This method includes issues with cost, hygiene, and reliability due to the presence of a liquid drain with a narrow diameter valve used in a toilet used to dispose of excrement. A better consumer toilet with a flow meter is needed.

SUMMARY

We disclose a novel device for measuring a volume of excrement added to a toilet. Measurements of excrement, including urine and feces, may be used to monitor a user's health. The device includes a liquid level sensor that may be a noncontact electrical impedance sensor. The liquid level sensor may be placed on the surface of a flush jet fill tube. The noncontact electrical impedance sensor measures changes in liquid flow rate through the flush jet fill tube over time. Because the toilet includes a hydrostatic circuit, changes in water being added to the toilet bowl through the flush jet fill tube are indicative of the volume that has been added to the toilet bowl.

The noncontact electrical impedance sensor may be a capacitor with two metal electrodes made of metal strips. The strips may be separated by a gap and may be wrapped at least partially around the outside surface of the flush jet fill tube or arranged along a direction of water flow on the surface of the flush jet fill tube.

The sensor on the flush jet fill tube may function with liquid sensors in other parts of the toilet, including the toilet bowl and the trap way to provide a more complete assessment of liquid movement through the toilet and volume addition by a user.

Some embodiments include a processor which performs tasks such as recording data from the liquid level sensor, combining this data with that collected from other sensors, and providing reports that may be relevant to a user's health status.

DETAILED DESCRIPTION

Definitions

Toilet, as used herein, means a device that may be used to collect one or more biological waste products of a user.

User, as used herein, means a human or animal that deposits bodily waste into an embodiment of the toilet disclosed herein.

Flush jet fill tube, as used herein, means a tube or pipe that is connected to a water system and which refills a toilet bowl with water after the toilet is flushed. The fill tube may also be called a refill tube.

Trap way, as used herein, means a section of pipe connecting the toilet bowl to a sewer pipe through which waste passes into the sewer system. The section of pipe is typically curved with the section nearest the toilet bowl holding water when the toilet bowl is full. The section nearest the sewer pipe does not hold water. The trap way may also be called a P-trap or S-trap.

Water seal, as used herein, means a vertical section of a trap way which holds water, the water acting as a barrier for sewer gases which would otherwise travel from a sewer pipe connected to the trap way into the toilet bowl.

Disclosed herein is a toilet capable of measuring small changes in volume within the toilet's hydrostatic circuit. The toilet accomplishes this task by measuring the flow rate of water traveling through the hydrostatic circuit. Specifically, the disclosed toilet comprises a noncontact electrical impedance sensor connected to a flush jet fill tube which detects small changes in volume within the toilet bowl. Consequently, the volume of human excrement, including urine, feces, vomit, or other bodily waste that is deposited into the toilet bowl is detected.

It will be readily understood that the components of the present invention, as generally described and illustrated in the Figures herein, could be arranged and designed in a wide variety of different configurations. Thus, the following more detailed description of the embodiments of the invention, as represented in the Figures, is not intended to limit the scope of the invention, as claimed, but is merely representative of certain examples of presently contemplated embodiments in accordance with the invention. The presently described embodiments will be best understood by reference to the drawings, wherein like parts are designated by like numerals throughout.

Figure 1:
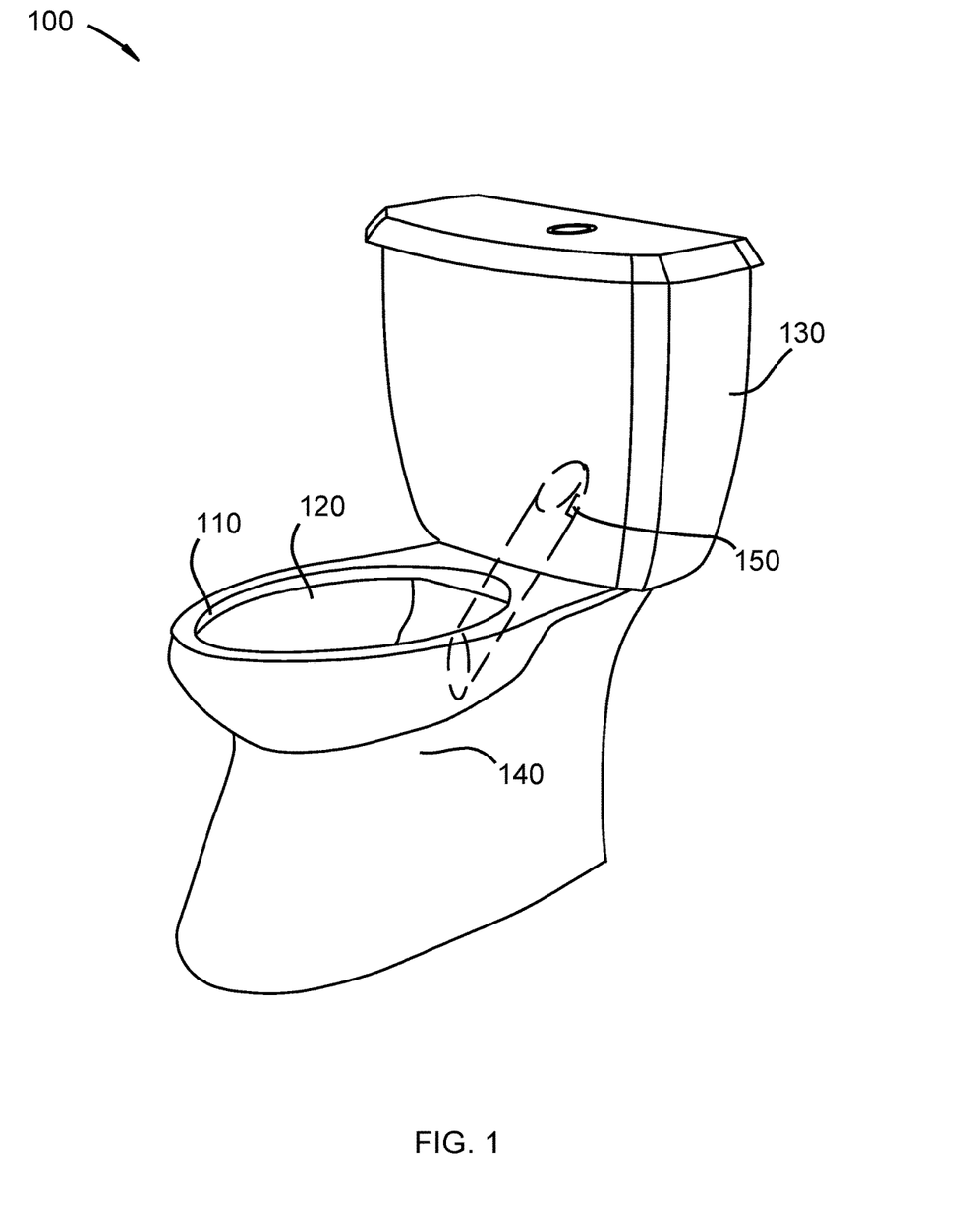
FIG. 1 is a perspective view of a toilet with a flush jet fill tube with a noncontact electrical impedance sensor within the fill tube.

Referring to FIG. 1, toilet 100 is illustrated which includes rim 110, toilet bowl 120, and tank 130. Additionally, toilet 100 includes flush jet fill tube 140 which is connected to a water source. When toilet 100 is flushed, water in toilet bowl 120, along with any excrement that is present, moves through a waste exit port in toilet bowl 120 and through a wastewater exit pipe. The wastewater exit pipe includes a curved trap system, sometimes referred to as a P-trap. The end of the trap system that is furthest from the toilet and nearest a sewer pipe includes a spillway. The spillway comprises a height corresponding to a maximum level of standing liquid in the toilet bowl.

Flush jet fill tube 140 includes liquid level sensor 150. Liquid level sensor 150, and other embodiments thereof, measures the level of liquid in flush jet fill tube 140 over time. While other embodiments are within the scope of the invention, liquid level sensor 150 is shown on the lower side of flush jet fill tube 140. One of skill in the art will recognize that other parts are included in a toilet, including additional plumbing which is connected to fill tube 140. These have been omitted from FIG. 1 for clarity.

While typical toilets refill up to the level set by the spillway in the trap way ensuring a 2-inch high water seal between the toilet bowl and the sewer pipe, the toilet according to the disclosed invention may include a water seal with a height that his greater than 2 inches. For example, the water seal may be approximately 2.25 inches or approximately 2.5 inches high. In this design, the bowl may refill to a level that is lower than the spillway and still have at least a 2-inch water seal as required for connection to a sewer system. For at least the reason that the toilet bowl has a lower volume of water, it is possible to detect small additions of volume to the bowl, as occur during typical urination and defecation events.

When the liquid level sensor detects a volume in the toilet bowl that is below the desired water level during refill after flushing, the liquid level sensor may actuate a refill controller. The refill controller may be a solenoid valve connected to a water supply or other mechanism known in the art. The refill controller may be connected to a water refill valve and cause a water refill valve to stop the flow of water into the toilet bowl when the liquid level sensor detects a desired level of water in the toilet bowl.

Figure 2A:
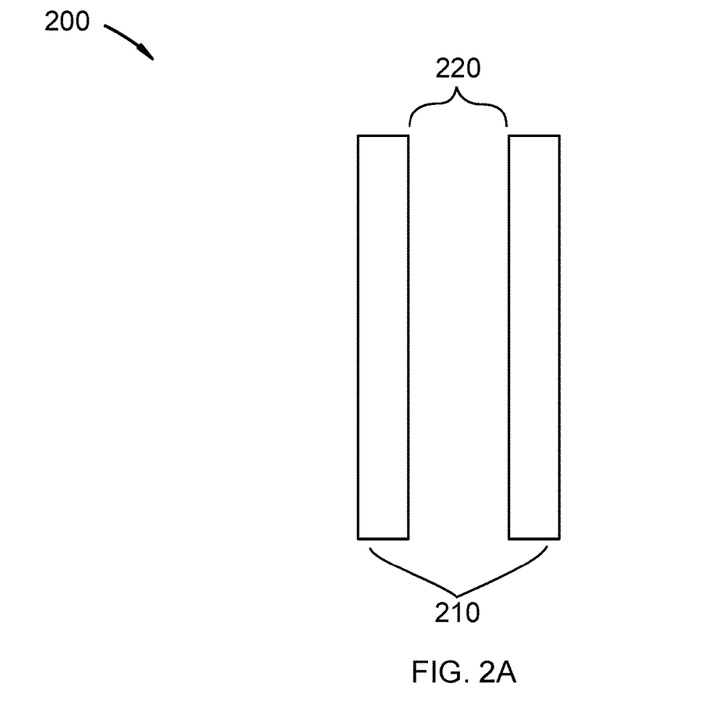
FIG. 2A is a schematic illustration of electrical strips according to an embodiment of the invention.
Figure 2B:
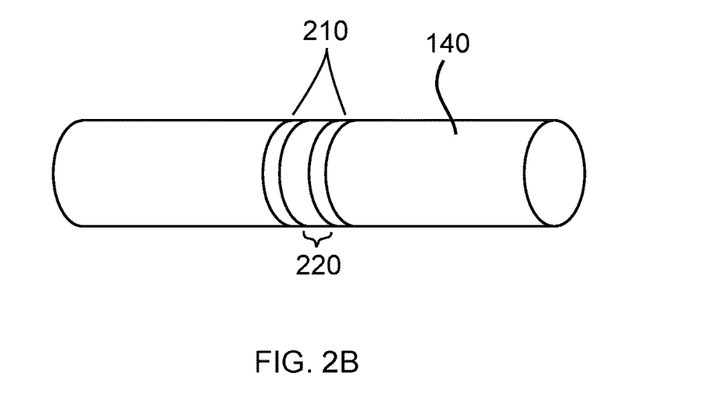
FIG. 2B is a schematic illustration of the electrical strips of FIG. 2A positioned on a flush jet fill tube.

FIGS. 2A and 2B illustrate an embodiment of the invention in which the liquid level sensor is a noncontact electrical impedance sensor. FIG. 2A is an illustration of an embodiment of such a sensor which is a capacitor. The capacitor includes capacitor plates 210 which are separated by gap 220. Capacitor plates 210 function as capacitively coupled electrodes and may be two substantially parallel metal strips. Capacitor plates 210 may be powered by an alternating current (AC) power source. The capacitor may be wrapped at least partially around the outside surface of the flush jet fill tube with the electrodes running perpendicular to the direction of water flow through the flush jet fill pipe as shown in FIG. 2B or arranged parallel with the direction of water flow through the flush jet fill tube.

In some embodiments, the capacitor is covered by an electrical shield. Some embodiments further include an insulating material. The insulating material may be placed between the electrical shield and the electrodes in a sandwich configuration. A clamp may secure the electrical shield against the insulating material. In some embodiments, the claim is circular and wraps at least partially around the circumference of the flush jet fill tube similar to a pipe clamp.

Figure 3:
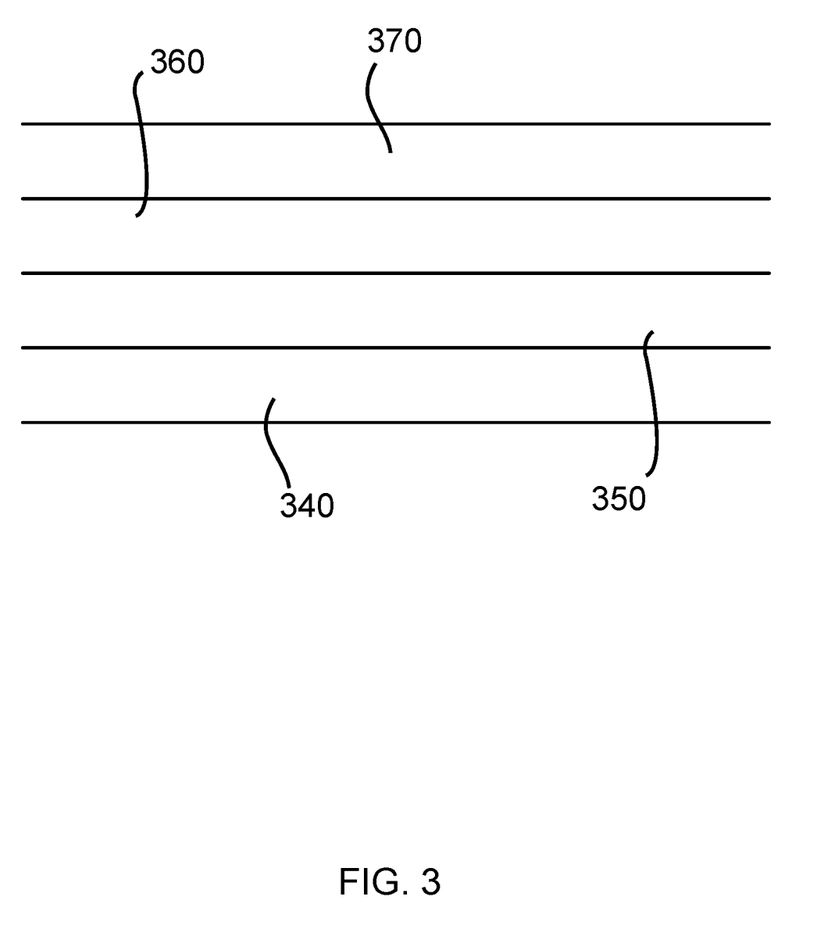
FIG. 3 is a cross section of a liquid level sensor including the electrodes, insulating material and electrical shield over a flush jet fill tube.

FIG. 3 illustrates the order of components in the sandwich configuration described above. Electrode 350 is placed against surface 340 of a flush jet fill tube. Insulating material 360 covers electrode 350. Electrical shield 370 then covers insulating material 360.

Given the electrical component of the liquid level sensor disclosed herein, embodiments are disclosed which inhibit a user from contacting the electrodes. In some embodiments the electrodes are placed on the side of the flush jet fill pipe that is furthest from the exterior surface of the toilet.

In some embodiments, the toilet includes a controller which may set the water level to a defined level in the toilet bowl. As in conventional toilets, the water level in the toilet bowl may be equal to or lower than the spillway water level to prevent the siphon activity from occurring and emptying the toilet bowl. The controller, thus, determines how much water will be added through the flush jet fill pipe after the toilet is flushed. Specifically, the controller receives a signal from the liquid level sensor on the flush jet fill pipe then actuates the flush jet fill tube to refill the toilet bowl to the appropriate water level.

In other embodiments, the toilet may also include a water level meter that may be located in one or both of the toilet bowl or spillway. The water level meter(s) may be a non-contact electrical impedance sensor or other type of water level sensor known in the art. The combination of liquid level sensor in the flush jet fill tube and water level meter in the toilet bowl and/or spillway may provide a more accurate assessment of volume change within the toilet bowl.

Figure 4:
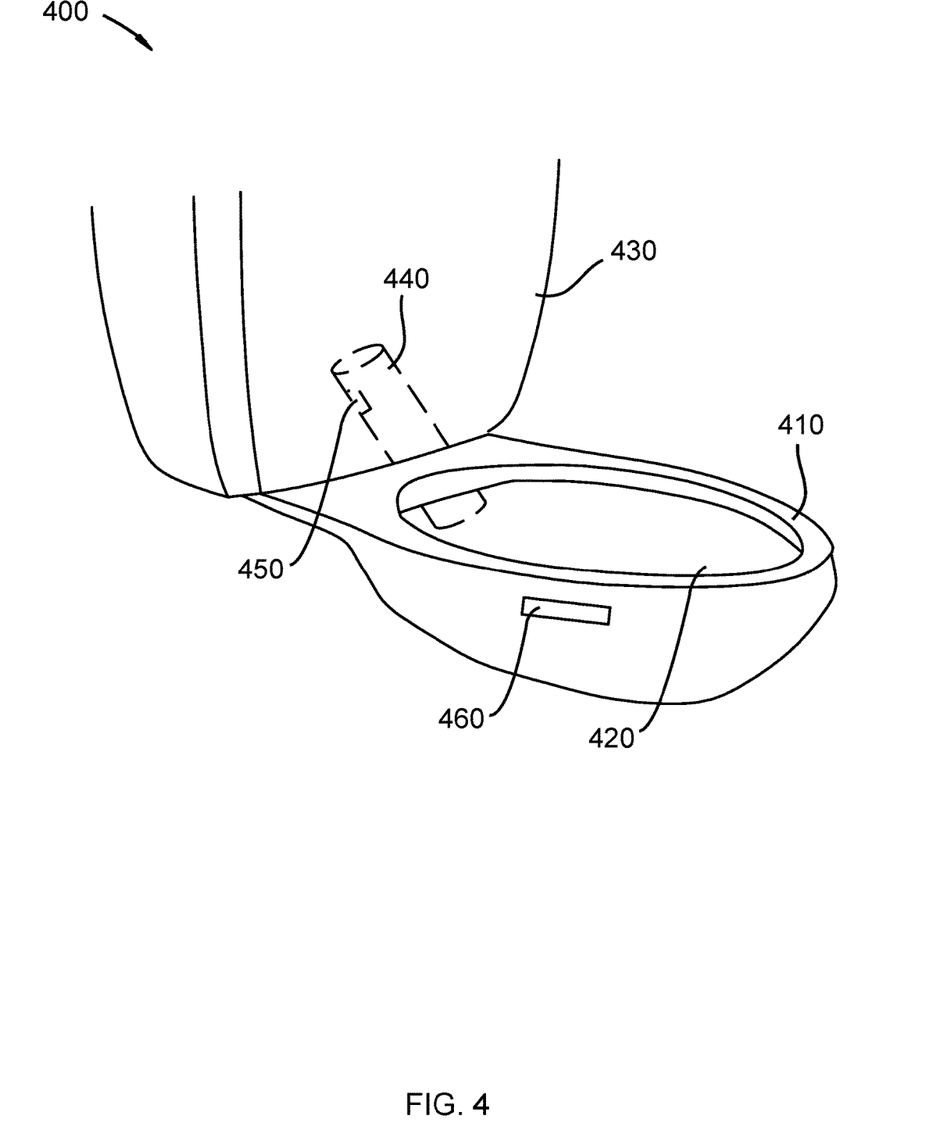
FIG. 4 is an embodiment of a toilet with a flush jet fill tube, a noncontact electrical impedance sensor within the fill tube, and a volume sensor in the toilet bowl.

FIG. 4 illustrates toilet 400, which is an embodiment of the invention. Similar to conventional toilets, toilet 400 comprises rim 410, toilet bowl 420, and tank 430. Unlike conventional toilets, toilet 400 further comprise flush jet fill tube 440 which includes liquid level sensor 450. Additionally, toilet 400 includes water level sensor 460 which, in this embodiment, is located within toilet bowl 420. In some embodiments, water level sensor 460 may be a noncontact electrical impedance sensor. By including two sensors in two different positions, a clearer indication of the volume of waste added to the toilet bowl may be obtained.

Figure 5:
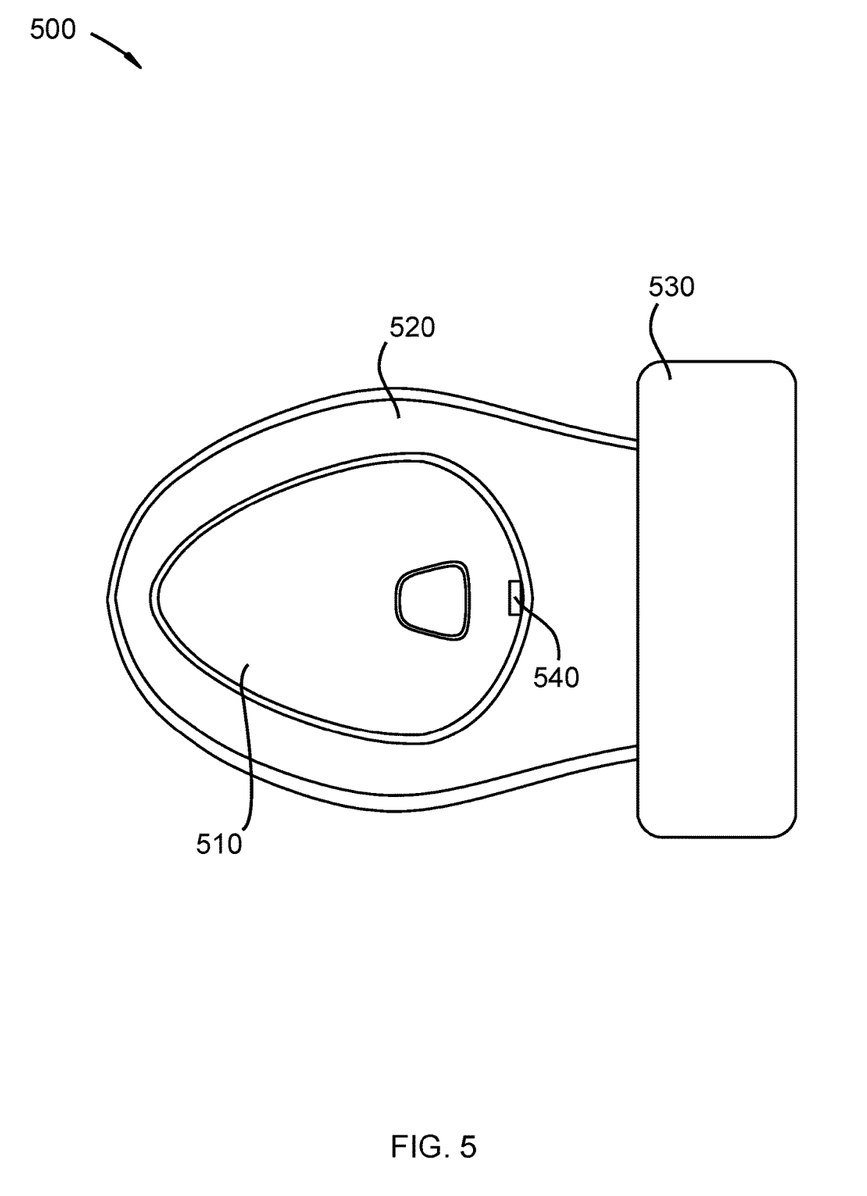
FIG. 5 is a top view of a toilet with a gas sensor according to an embodiment of the invention.

FIG. 5 is a downward-looking illustration of toilet 500, another embodiment of the disclosed invention. Toilet 500 includes toilet bowl 510, rim 520, and tank 530. Toilet 500 further includes gas sensor 540. Gas sensor 540 detects volatile organic compounds (VOCs) which may be produced by flatulence or from fecal matter that has been deposited in the toilet bowl by a user after a bowel movement. Gas sensor 540 and other embodiments thereof may be used in combination with the flush jet fill tube and liquid level sensor as disclosed herein to determine whether a user has had a bowel movement or whether the VOCs detected by a gas sensor are from other sources. For example, when a user has had a bowel movement and deposited fecal matter into the toilet bowl, the gas sensor may detect VOCs and the liquid level sensor may detect an increase in volume within the toilet bowl. Alternatively, when a user has experienced flatulence without an accompanying bowel movement, the gas sensor may detect VOCs but the liquid level sensor may detect no increase in volume within the toilet bowl. The water level sensor illustrated in toilet 400 of FIG. 4 as well as other embodiments of the disclosed invention may also be combined with a gas sensor. In addition, in embodiments of the toilet that include a blood pressure monitor, the blood pressure monitor may identify changes in blood pressure that are indicative of exertion during the bowel movement.

Figure 6:
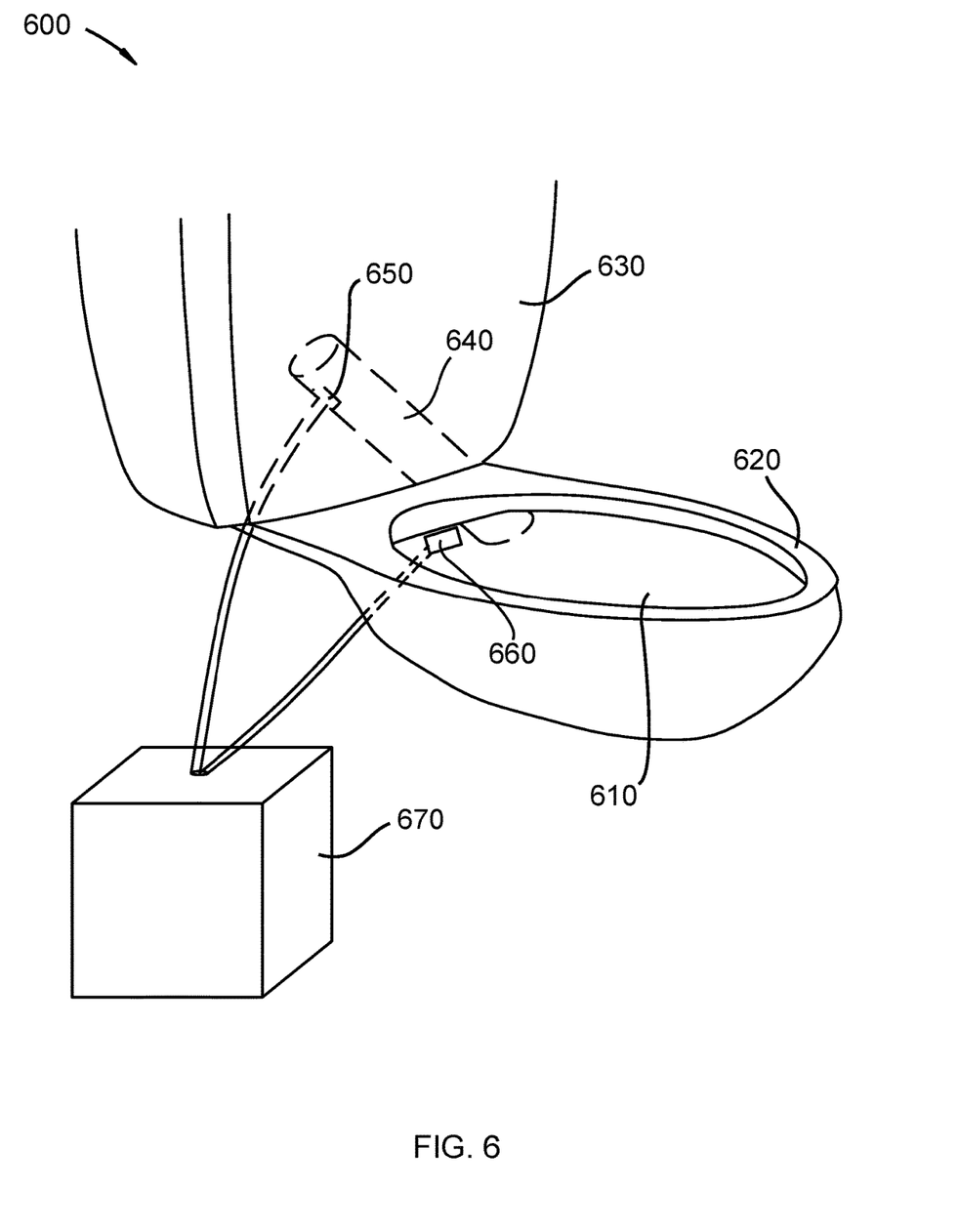
FIG. 6 is a perspective view of a toilet with a flush jet fill tube, a noncontact electrical impedance sensor, a gas sensor, and a processor according to an embodiment of the invention.

FIG. 6 illustrates toilet 600, yet another embodiment of the disclosed invention. Like conventional toilets, toilet 600 includes rim 620, toilet bowl 610, and tank 630. Toilet 600 further includes flush jet fill pipe 640, liquid water sensor 650, and gas sensor 660. Toilet 600 also includes processor 670 which records and processes signals collected by liquid level sensor 650 and gas sensor 650. Processor 670 may be a microcontroller (MCU) or other electronic controller. Changes in the volume present in toilet bowl 610 and VOCs detected by gas sensor 650 may be recorded and reported by processor 670. Health data may be calculated from signals that enter processor 670 for use by healthcare professionals who may be tasked with monitoring or diagnosing the health status of the user. Lines shown in FIG. 6 which connect both liquid level sensor 650 and gas sensor 650 to processor 670 indicate signal input which may be through wireless connection, through electrical wiring, or methods for transferring data to a processor that are known in the art.

Because the liquid level sensor measures changes in volume over time, the processor in the toilet may also record the change in volume in the toilet bowl over time and perform calculations and create reports that are useful in assessing the user's health status. For example, the processor may calculate and report a user's urine flow rate. Due to the temporal nature of the liquid level measurement, the processor may also report irregular urine flow rate. This is especially useful in monitoring or diagnosing an enlarged prostate. Some embodiments also include a blood pressure monitor. Combining measurements of urine flow rate with measured changes in blood pressure may estimate urinary exertion which is also an indicator of prostate health.

Because adding solid matter displaces water in the toilet bowl, the liquid level sensor may also determine the volume of a user's solid feces after a bowel movement. Likewise, the processor may calculate and report the volume of the user's feces.

Furthermore, in combination with a gas sensor, the processor may determine that a user has diarrhea and record how much fluid has been lost. Specifically, the gas sensor may detect VOCs while the liquid level sensor detects a flow rate that is consistent with liquid being deposited into the toilet as opposed to solid fecal matter. The processor may differentiate between liquid and solids being added to the toilet by receiving a signal from the liquid level sensor that indicates a consistent increase in volume (added liquid) as compared to a sudden increase in volume (added solid material). The volume of fluids lost as diarrhea may be an important clinical data point. Such information may alert the user to contact a healthcare provider because too much fluid has been lost.

Embodiments of the invention what include a processor may be used to detect possible clogs or partial clogs in the toilet. The processor may determine when the toilet has been flushed. when a flush is accompanied by an abnormal change in the level of liquid in the flush jet fill tube over time. A report of a potential clog could alert a user to perform maintenance before the clog worsens.

While specific embodiments have been illustrated and described above, it is to be understood that the disclosure provided is not limited to the precise configuration, steps, and components disclosed. Various modifications, changes, and variations apparent to those of skill in the art may be made in the arrangement, operation, and details of the methods and systems disclosed, with the aid of the present disclosure.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art that changes may be made to the details of the above-described embodiments without departing from the underlying principles of the disclosure herein.

We claim:

1. A toilet comprising:
   a flush jet fill tube;
   a toilet bowl, wherein the toilet bowl comprises a flush jet entrance port and a waste exit port;
   a wastewater exit pipe, wherein the wastewater exit pipe comprises a trap system; and
   a liquid level sensor comprising a noncontact electrical impedance sensor, wherein the noncontact electrical impedance sensor comprises a capacitively coupled electrode or electrodes and an alternating current power source providing alternating current electrical power to the electrode or electrodes;
   wherein the liquid level sensor measures the level of liquid in the flush jet fill tube over time, and
   wherein the electrode or electrodes comprise of two substantially parallel metal strips, wherein the strips are separated by a gap, wherein the strips wrap at least partially around an outside surface of the flush jet fill tube or are arranged parallel with a direction of water flow on the surface of the flush jet fill tube.

2. The toilet of claim 1, further comprising an electrical shield, the electrical shield covering the electrode or electrodes.

3. The toilet of claim 2, further comprising:
   an insulating material, the insulating material is positioned against the electrical shield and disposed between the electrical shield and the electrode or electrodes.

4. The toilet of claim 1, wherein the toilet further comprises an exterior surface, and wherein the flush jet fill tube comprises:
   a. a first side, wherein the first side is closest to the exterior surface; and
   b. a second side, wherein the second side is furthest from the exterior surface; and
   c. wherein the electrode or electrodes are disposed on the second side to avoid contact with a user's body.

5. The toilet of claim 1, wherein the toilet further comprises a controller, wherein the controller:
   a. sets a water level in the toilet bowl after a flush;
   b. actuates the flush jet fill tube to refill the toilet bowl to the water level; and
   c. receives signals from the noncontact electrical impedance sensor.

6. The toilet of claim 1, further comprising:
   a gas sensor, wherein the gas sensor measures volatile organic compounds; and
   a processor.

7. The toilet of claim 6, wherein the processor determines either that:
- a user has deposited fecal matter into the toilet bowl when the gas sensor detects volatile organic compounds and the liquid level sensor detects an increase in volume within the toilet bowl or,
- a user has emitted flatulence without depositing fecal matter into the toilet bowl when the gas sensor detects volatile organic compounds and the liquid level sensor detects no increase in volume within the toilet bowl.

8. The toilet of claim 6, wherein the processor determines that a user has diarrhea when the gas sensor detects volatile organic compounds and the liquid level sensor detects a flow rate that is consistent with liquid being deposited into the toilet as opposed to solid fecal matter.

9. The toilet of claim 1, further comprising a processor, wherein the processor detects that the toilet has been flushed and reports a potential clog when a flush is accompanied by an abnormal change in the level of liquid in the flush jet fill tube over time.

\* \* \* \* \*